United States Patent [19]

Jones

[11] Patent Number: 5,007,457

[45] Date of Patent: Apr. 16, 1991

[54] PNEUMATIC OSCILLATORS

[75] Inventor: Norman S. Jones, Stanbridge, England

[73] Assignee: Instruments and Movements Limited, London, England

[21] Appl. No.: 556,303

[22] Filed: Jul. 20, 1990

Related U.S. Application Data

[63] Continuation of Ser. No. 352,962, May 17, 1990, abandoned.

[30] Foreign Application Priority Data

May 20, 1988 [GB] United Kingdom ............... 8812004

[51] Int. Cl.$^5$ .............................................. F16K 1/32
[52] U.S. Cl. ............................ 137/624.14; 251/333; 251/284
[58] Field of Search ..................... 137/624.14, 516.29; 251/284, 332, 333, 357

[56] References Cited

U.S. PATENT DOCUMENTS 3,216,328 11/1965 Peterson .
3,667,502 6/1972 Otto .
3,881,480 5/1975 Lafourcade .
4,140,148 2/1979 Richter .

FOREIGN PATENT DOCUMENTS 1530478 6/1968 France .
1533550 11/1978 United Kingdom .

Primary Examiner—Alan Cohan
Attorney, Agent, or Firm—Arnold B. Silverman; David V. Radack

[57] ABSTRACT

A pneumatic oscillator especially useful for generating breathable gas pulses in a resuscitator and/or lung ventilator device has a reciprocable piston or equivalent controlling a poppet valve arrangement that includes a sealing lip coacting with a resilient facing. The sealing lip provides for sharp definition of a line of contact on the resilient facing and penetration of the latter by the lip is limited by stop means, preferably abutment(s) coacting with the facing adjacent to the line of contact with the sealing lip. This prevents wear and/or excessive indentation of the facing with consequent shift of the contact line and alteration of the oscillator characteristic with time.

7 Claims, 1 Drawing Sheet

PNEUMATIC OSCILLATORS

This is a continuation of application Ser. No. 07/352,962, filed May 17, 1990, now abandoned.

BACKGROUND OF THE INVENTION

1. Field of the Invention

This invention concerns pneumatic oscillators, especially but not exclusively for the operation of resuscitators and/or ventilators and like devices for inducing or assisting lung function in human patients.

2. Background Discussion

In general, such devices generate a train of pulses of breathable gas that is ducted to a patient, usually via a so-called patient valve and/or an oronasal mask or tracheal intubation device. The generation of the pulse train with pulses at the required intervals and with appropriate tidal flow characteristics requires some form of switching mechanism controlling the flow of breathable gas from a source to the pulse output. Simplicity, reliability and constancy of performance in service, and robustness are dominant criteria in the design of resuscitators or ventilators, especially those intended for use by emergency services such as ambulance crews, or for use in a domestic environment by non-specialist operators.

3. The Prior Art

Pneumatic oscillators exist in various forms and many forms have been applied to this purpose. GB-A-1 533 550 exemplifies one such form of pneumatic oscillator that has been successfully applied in practice but even that oscillator comprises several components and several moving parts, with consequent complexity and cost.

In another form of pneumatic oscillator, a piston or its equivalent is reciprocable to open and close a flow path between a source of pressurized breathable gas and a pulse output. The piston is biassed towards the flow path-closing position and the biassing is supplemented by gas pressure derived from the output of the device. Source gas pressure is applied to the piston in a manner to overcome the biassing so as to cause the piston to move to its flow path-opening position; whereupon the device outputs a gas pressure pulse from which pressure is derived to supplement the biassing and restore the piston to its flow path-closing position. Examples of such an oscillator are disclosed in FR-A-1 530 478 and US-A-3 881 480.

To obtain a snap-action in the opening and closing of the flow path, a poppet valve arrangement is utilised in which a sealing lip coacts, in the flow path-closing condition, with a resilient facing in such a manner as to isolate an area of the piston or equivalent from the gas pressure acting elsewhere. Accordingly, when the flow path is open, gas pressure is applied to a different area than when the flow path is closed with the consequence that there is an abrupt change of effective area exposed to gas pressure at the point of switching, and an abrupt change in the force balance on the piston.

Although an oscillator of this general form exhibits remarkable simplicity and would appear to be eminently suitable for the applications considered, in practice such oscillators have not achieved widespread adoption because the attainment of accurate and reproducible performance characteristic depends critically upon the maintenance of close tolerances in manufacture and even then the characteristics tend to change, unpredictably, in service. The reason for this is that the characteristics are critically affected by the force balance on the piston or its equivalent at the point of switching and this in turn is influenced by a number of factors. One such factor is the relative areas of piston or equivalent exposed to gas pressure at the point of switching, as determined by engagement of the sealing lip of the poppet valve with its resilient facing.

For a good snap-action it is essential that there is minimal leakage across this seal right up to the point of force balance and that at this point, the flow path is opened suddenly and with a force/flow gap characteristic that is stable over long periods and is unaffected by wide ranges of temperatures and duty patterns. There is as a consequence a conflict of design requirements because to obtain good sealing (low leakage) the combination of a resilient facing and a sharply defined lip is desirable. However this combination leads to permanent set indentation and/or cutting of the facing material in service, with consequent deterioration of performance. Accordingly it is usual to depart from the ideal configuration for low leakage by employing a more rounded sealing lip. While this provides good sealing over long periods of service and avoids cutting of the facing material, it brings with it the disadvantage that the line of contact between the lip and the facing material is not sharply defined and varies in service as a result of the facing material becoming permanently indented. Thus the area within the lip tends to change during service and so alter the ratio of the areas that control the force balance at the point of switching.

SUMMARY OF THE INVENTION

In accordance with the invention a pneumatic oscillator of the form discussed is characterised by a poppet valve arrangement that incorporates a sealing lip providing for sharp definition of a line of contact on a resilient facing to define a switching control area and stop means adapted to limit penetration of the facing by the lip in the flow path-closing condition.

Preferably the stop means are associated with the sealing lip and are disposed to coact with the facing adjacent to the line of contact of the sealing lip.

The stop means may take various forms. Preferred forms comprise a ring of castellations concentric with the lip and outboard or inboard thereof so that symmetry is obtained, without the stop means interfering with exposure of the areas outboard and inboard of the lip to operating gas pressures.

BRIEF DESCRIPTION OF THE DRAWINGS

The invention is further explained with reference to the accompanying drawings in which.

DESCRIPTION OF THE PREFERRED EMBODIMENTS

Figure 1:
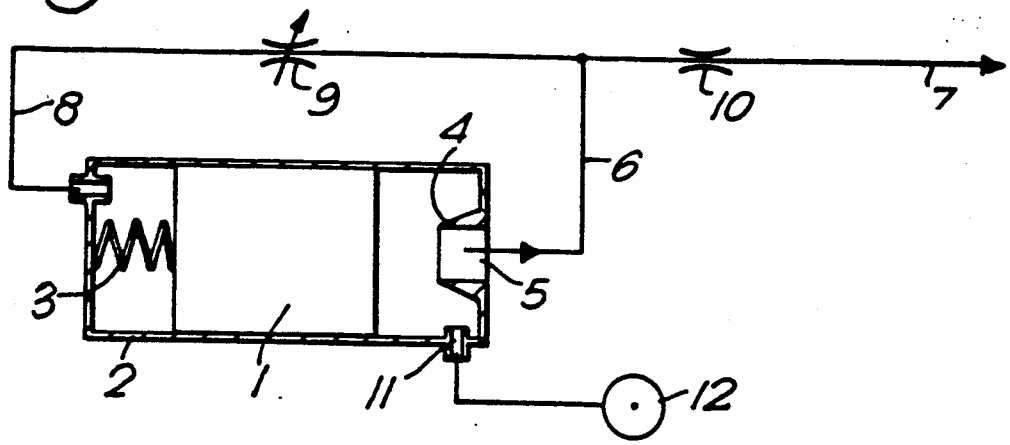
FIG. 1 illustrates diagrammatically the principles of a pneumatic oscillator of the form to which the invention pertains.

The principle of an oscillator of the form to which the invention is applicable is illustrated diagrammatically in FIG. 1 of the drawings. A piston 1 is reciprocable in a cylinder 2 and is biassed by a spring 3 towards the right as seen in the drawing, to engage a sealing lip 4 surrounding a port 5 in the end of the cylinder 2. In the arrangement shown the port 5 constitutes an outlet port connected to an output line 7 by way of an outlet branch 6.

The outlet branch 6 also connects with a feedback line 8 via a restrictor 9, the feedback line 8 connecting with the end of the cylinder opposite to that containing the port 5. A further restrictor 10 is interposed between the outlet branch 6 and the output line 7.

A further port 11 in the end of the cylinder 2 and outboard of the port 5 serves for the admission of pressurized breathable gas, for instance compressed air or oxygen, to this end of the cylinder 2.

The drawing shows the piston 1 in a flow path-opening position clear of the sealing lip 4. In this position of the piston 1, breathable gas can flow from the source indicated at 12 via the ports 11 and 5 to the outlet branch 6 and thence via the restrictor 10 to the output line 7 and also via the restrictor 9 and the feedback line 8 to the left hand end of the cylinder 2 as seen in the drawing. As a consequence of the flow of gas in the branch 6 and the presence of the restrictor 10, gas flows through the feedback line to the left hand end of the cylinder 2 at a rate controlled by the restrictor 9 and builds up pressure therein that acts on the piston 1 to supplement the force of the spring 3. Eventually the combined effects of the gas pressure and spring 3 cause the piston to move to the right as seen in the drawing, towards the sealing lip 4. As the piston approaches the latter, flow to the outlet branch 6 is restricted and the pressure therein drops so that there is a sudden shift in the balance of forces on the piston 1 and this completes its movement to the right with a snap-action, to engage the sealing lip 4 and thus cut off flow to the port 5 and outlet branch 6.

Pressure in the left hand end of the cylinder 2 then decays by reverse flow of gas from the cylinder through the feedback line and restrictors 9 and 10. When the gas pressure in the left hand of the cylinder 2 has decayed to an appropriate extent, the source gas pressure acting on the annular area of the piston 1 outboard of the sealing lip 4, overcomes the force of the spring 3 and causes the piston 1 to commence to move towards the left as seen in the drawing. As it does so, it opens the pathway to the port 5 and gas flows into the outlet branch 6, building up pressure therein which acts on the central area of the piston 1 to supplement the thrust of the source pressure on the outboard annular area of the piston. There is in consequence an abrupt change in the balance of forces acting on the piston 1 which moves with a snap-action to the position shown in the drawing, whereupon the described cycle repeats with a frequency determined by the relationship between the annular area outboard of the sealing lip 4 and the total cylinder area, the bias force supplied by the spring 3 and the characteristics of the restrictors 9 and 10.

The principles of the operation of this form of pneumatic oscillator may be embodied in various arrangements in practical devices. For instance the restrictor 9 may be replaced by various restrictor/non-return valve networks to achieve particular cycling patterns in the output line and to provide different operator control possibilities. The biassing of the piston may be achieved by means other than a spring: for instance the piston may have different areas effective at its opposite ends so that when both ends of the piston are exposed to equivalent pressures it experiences a net thrust towards the flow path-closing position. The piston may be replaced by one or more diaphragms. Whereas in the arrangement shown the port 5 constitutes an outlet port and the port 11 constitutes an inlet, the converse arrangement is possible. Moreover, the sealing lip 4 may be carried by the piston (or its equivalent) to move therewith and coact with a resilient facing on the cylinder end wall, instead of being carried by the latter as in the illustrated arrangement.

Figure 2:
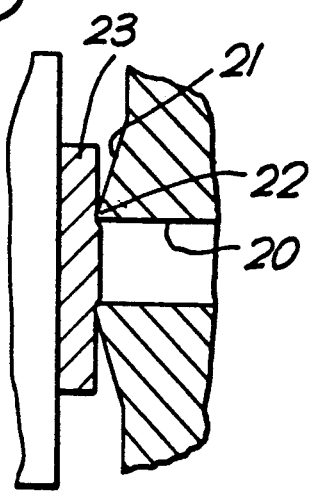
FIG. 2 illustrates a typical poppet valve arrangement as hitherto used in such an oscillator.
Figure 3:
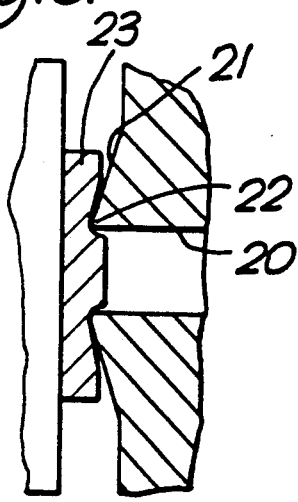
FIG. 3 illustrates the effect of wear and extended service upon the configuration of the typical poppet valve arrangement illustrated by FIG. 2.

FIG. 2 illustrates a typical poppet valve arrangement in which a sealing lip is defined by an inner cylindrical surface 20 merging with an outer conical surface 21 in a rounded lip surface 22 of relatively small radius chosen to avoid cutting of the resilient facing material 23 under the loads experienced in service. However as a consequence of extended service and as shown in FIG. 3, the facing material 23 takes a permanent indentation or set such that the effective line of contact between the sealing lip and the facing material moves outwardly around the lip surface 22 and towards a point on the surface 21. This has the effect of changing both the inner and the outer effective areas defined by the sealing lip.

For instance if in a new poppet valve the contact line is a circle of diameter 7 mm, the area within the contact line is $$\frac{\pi \times 7^2}{4} \text{ mm}^2.$$

If in service the resilient facing material wears or indents to change the position of the line of contact by as little as 0.1 mm radially, the area within the line of contact becomes $$\frac{\pi \times (7.1)^2}{4} \text{ mm}^2,$$

a change of about 6%. This change in a typical oscillator controlling a resuscitator or ventilator could result in a change of the allowed exhalation time in excess of 10%, which change is unacceptable for most applications.

Figure 4:
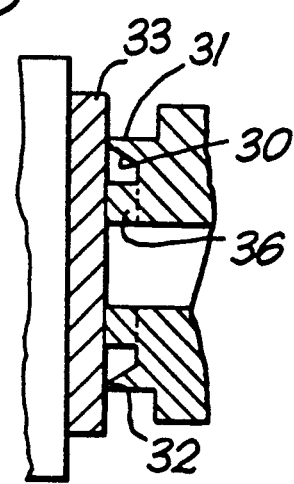
FIG. 4 illustrates a poppet valve arrangement for an oscillator embodying the invention.
Figure 5:
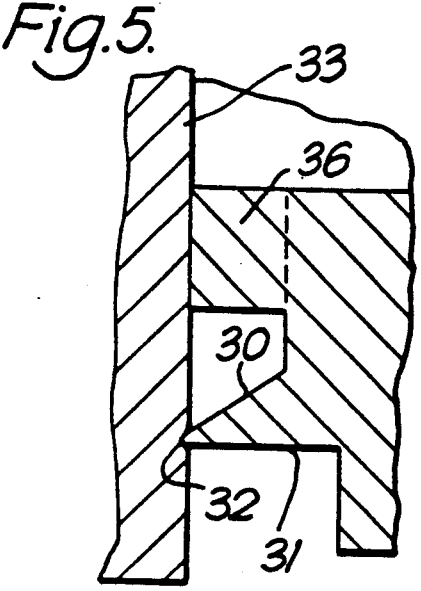
FIG. 5 illustrates on an enlarged scale the nature of the contact between the sealing lip and the facing material in the flow path-closing condition of the poppet valve.

FIGS. 4 and 5 illustrate the design of a preferred form of poppet valve for an oscillator embodying the present invention. In the poppet valve illustrated in these Figures the sealing lip has a sharp lip surface 32 defined by the junction between inner and outer surfaces 30, 31 disposed with a small included angle. In the illustrated arrangement the outer surface is that of a circular cylinder whereas the inner surface 30 is conical but the converse arrangement can be adopted as can an arrangement in which both inner and outer surfaces are inclined to the axis. However, for best effect the surface on the gas supply side of the lip should be as close to the cylindrical form as practicable.

In accordance with the invention the sealing lip is associated with stop means arranged to limit movement of the sealing lip towards the facing 33 so as to restrict penetration of the facing by the sealing lip, to a predetermined allowable extent.

The stop means may take various forms and may comprise one or more abutments associated with parts carrying the sealing lip and the facing respectively. However it is preferred that the stop means be associated with the sealing lip in a manner to coact with the facing adjacent to the line of contact between the sealing lip and the facing, this arrangement providing the closest control over the penetration of the sealing lip into the facing.

There may be a single abutment associated with the sealing lip but it is preferred, for reasons of symmetry and load distribution, to utilise a plurality of abutments arranged in a ring concentric with the sealing lip.

Thus in the arrangement illustrated in FIGS. 4 and 5, the sealing lip is associated with a ring of castellations 36 concentric with the sealing lip and, in this embodiment, arranged inboard of the latter. However an outboard disposition of the stop means is also feasible. There could be two rings of abutments or castellations, for instance one inboard and the other outboard of the sealing lip.

Preferably the stop means is disposed to coact with the facing in an area thereof that is not active in the switching function, so that any masking of that area by the stop means does not affect the switching function. Moreover, the stop means, While having a contact area that is large in relation to that of the sealing lip, preferably has a contact area that is small in relation to the contact area of the facing region that it engages.

In other embodiments of the invention, the stop means may comprise one or more continuous surfaces concentric with but spaced radially from the sealing lip. However to avoid unwanted effects of masking of the intervening area of the facing, and of gas flows through the small gap between a stop means surface and the facing at the point of switching, gas flow pathways would preferably be provided between the areas inboard and outboard of a continuous stop means surface.

I claim:

1. A pneumatic oscillator comprising a reciprocable piston or equivalent operating a poppet valve arrangement including a port to control a gas flow path from a gas source to a gas outlet, said poppet valve arrangement biassed to the path-closing condition with feedback of gas pressure at said gas outlet to supplement the bias in opposition to source pressure at the poppet valve, said poppet valve arrangement having a sealing lip providing for sharp definition of a line of contact on a resilient facing to define a switching control area, and stop means adapted to limit penetration of the facing by the lip in the flow path-closing condition, said stop means being positioned to engage said resilient facing downstream of said switching control area.

2. An oscillator according to claim 1, wherein said stop means are associated with the sealing lip and are disposed to coact with the facing adjacent to the line of contact of the sealing lip.

3. An oscillator according to claim 2, wherein said stop means comprise a continuous abutment surface parallel with the sealing lip.

4. An oscillator according to claim 3, wherein said sealing lip provides a circular line of contact with the facing and said abutment surface is concentric therewith.

5. An oscillator according to claim 4, wherein said abutment surface is discontinuous and provided by a ring of castellations.

6. An oscillator according to claim 4, wherein said abutment surface is continuous and there is provision for gas flow between regions of the facing inboard and outboard of the abutment surface when the latter abuts the facing.

7. An oscillator according to claim 2, wherein said stop means comprise a discontinuous abutment surface parallel with the sealing lip.

* * * * *